(12) United States Patent
McGlothlin et al.

(10) Patent No.: US 10,569,451 B1
(45) Date of Patent: Feb. 25, 2020

(54) VULCANIZATION OF DIP-MOLDED RUBBER ARTICLES WITH REDUCED MOLTEN MEDIA BATH TIMES

(71) Applicants: Mark W. McGlothlin, San Diego, CA (US); Scott Herrick, Escondido, CA (US)

(72) Inventors: Mark W. McGlothlin, San Diego, CA (US); Scott Herrick, Escondido, CA (US)

(73) Assignee: Apex Medical Technologies, Inc., San Diego, CA (US)

( * ) Notice: Subject to any disclaimer, the term of this patent is extended or adjusted under 35 U.S.C. 154(b) by 0 days.

(21) Appl. No.: 15/958,821

(22) Filed: Apr. 20, 2018

Related U.S. Application Data

(62) Division of application No. 15/602,041, filed on May 22, 2017, now abandoned.

(51) Int. Cl.

| | | |
|---|---|---|
| *B29C 41/46* | (2006.01) | |
| *A61F 6/04* | (2006.01) | |
| *A61B 42/10* | (2016.01) | |
| *C08L 75/04* | (2006.01) | |
| *C08L 11/02* | (2006.01) | |
| *C08L 7/02* | (2006.01) | |
| *B29C 41/14* | (2006.01) | |
| *B29C 41/42* | (2006.01) | |
| *B29C 35/04* | (2006.01) | |
| *B29C 71/02* | (2006.01) | |
| *B29L 31/48* | (2006.01) | |
| *B29L 31/00* | (2006.01) | |
| *B29K 75/00* | (2006.01) | |
| *B29K 7/00* | (2006.01) | |
| *B29K 9/00* | (2006.01) | |
| *B29K 105/00* | (2006.01) | |

(52) U.S. Cl.
CPC ............. *B29C 41/46* (2013.01); *A61B 42/10* (2016.02); *A61F 6/04* (2013.01); *B29C 35/045* (2013.01); *B29C 41/14* (2013.01); *B29C 41/42* (2013.01); *C08J 7/08* (2013.01); *C08L 7/02* (2013.01); *C08L 11/02* (2013.01); *C08L 75/04* (2013.01); *B29C 2035/048* (2013.01); *B29K 2007/00* (2013.01); *B29K 2009/00* (2013.01); *B29K 2011/00* (2013.01); *B29K 2075/00* (2013.01); *B29K 2105/0064* (2013.01); *B29L 2031/4864* (2013.01); *B29L 2031/7538* (2013.01); *C08J 2321/02* (2013.01)

(58) Field of Classification Search
CPC ...... B29C 34/014; B29C 35/048; B29C 41/14
See application file for complete search history.

(56) References Cited

U.S. PATENT DOCUMENTS

| | | | |
|---|---|---|---|
| 6,569,375 B1 * | 5/2003 | McGlothlin | ............... C08J 5/02 264/236 |
| 2004/0022980 A1 * | 2/2004 | Mukherjee | ............... C08J 7/047 428/36.8 |
| 2005/0031884 A1 * | 2/2005 | Koide | ..................... B29C 33/56 428/521 |

\* cited by examiner

*Primary Examiner* — Robert C Boyle
(74) *Attorney, Agent, or Firm* — Trevor Coddington; Insigne LLP

(57) ABSTRACT

Pore-free rubber articles are prepared by dip-molding in a dipping medium that includes a vulcanizing agent, then partially-cured by immersing the dip former in a heated liquid bath that is chemically inert. A particularly effective liquid bath is a molten, nitrite free inorganic salt. The partially-cured rubber is then maintained at a desired curing temperature in a low/no oxygen heating oven to complete curing. Alternatively, upon removal from the molten salt bath, the latex film is quenched.

16 Claims, No Drawings

VULCANIZATION OF DIP-MOLDED RUBBER ARTICLES WITH REDUCED MOLTEN MEDIA BATH TIMES

BACKGROUND OF THE INVENTION

1. Field of Invention

The invention lies in the field of dip-molded rubber articles, and more particularly to methods of vulcanization of dip-molded rubber articles.

2. Description of Related Art

Natural rubber latex has been extensively used as a material of construction for elastomeric dip-molded medical devices and medical device components. Examples of medical devices and components made from natural rubber latex are surgical gloves, examination gloves, finger cots, catheter balloons, uterine thermal ablation balloons, catheter cuffs, condoms, contraceptive diaphragms, indwelling urinary drainage catheters, and male external urinary drainage catheters. Other examples will be apparent to those skilled in medicine and in the manufacture and use of these and similar medical devices. Dip-molding techniques are also used in making elastomeric devices for non-medical uses. These include toy balloons, industrial gloves, household gloves, and other similar devices. These devices, both medical and non-medical, can also be formed from synthetic rubber latex materials rather than natural rubber. In some cases, synthetic materials are preferred, for example where natural rubber is deemed unsuitable for some reason, e.g., allergic reaction, or where the synthetic material offers an advantage. U.S. Pat. No. 6,329,444 to McGlothlin et al., the entire disclosure of which is incorporated herein, addresses the use of synthetic cis-1,4-polyisoprene in making medical and non-medical devices.

In latex dip-molding processes, dip formers are dipped in a latex bath, then withdrawn from the bath, and then typically dried and vulcanized in hot air. Vulcanization is the process of transforming an uncurred rubber compound into a highly elastic product by forming a three-dimensional cross-linked network structure in the rubber matrix. In some cases, the latex is pre-vulcanized; i.e., the rubber particles in the latex are partially or fully vulcanized prior to the dipping step. A prevulcanized latex produces a film with improved wet and dry gel strengths, and when further vulcanization is performed after dipping and hot air drying, the tensile properties are improved. An advantage of prevulcanization is a reduction in the process time by lessening or eliminating the time required for the post-dip vulcanization. In some dip-molding processes, a chemical coagulant is included in the latex or on the dip former, and heat-sensitized coagulant dipping methods are applied to produce articles having a greater film thickness. Multiple dips are also used in some processes. Vulcanization performed on the latex film after the dip former is removed from the latex bath serves to form covalent bonds both within the individual rubber particles and between coalesced rubber particles. A problem with vulcanization both at this stage and prior to the dip is that the outer surfaces of the particles have greater exposure to the vulcanizing agents than the particle interiors, resulting in a case-hardening effect and a lack of uniformity in the rubber.

In dip-molding processes for rubber lattices, sulfur is often used as a vulcanizing agent, although various accelerators, activators, sulfur donors, and boosters are frequently included as well to optimize the process. The application of sulfur forms sulphidic cross-links between elastomer chains. In sulfur-based curing systems, the avoidance of reversion and toxicity are often considerations.

An alternative means of prevulcanization of latex by free radical crosslinking involves the use of organic peroxides and hydroperoxides. Latex that is prevulcanized with these materials is referred to as "peroxide vulcanized natural rubber latex" (PVNRL). Peroxide curing forms carbon-carbon bonds. Utilization of this process on a commercial scale requires large and expensive heated pressure vessels, and prevulcanization is a necessary part of the process.

"Continuous vulcanization in liquid baths" (LCM Vulcanization) is used on extruded rubber profiles. In LCM Vulcanization, a solid constant profile shape is extruded, then submerged in a hot liquid bath such as molten salt, hot oil, or melted lead, or in a hot fluid medium such as fluidized sand particles. Essentially all molecular oxygen is excluded from the curing environment. The use of the hot liquid bath or fluid medium is to provide very rapid heat transfer rates to thin-wall extruded rubber profiles. U.S. Pat. Nos. 6,569,375; 6,775,848; and 6,920,643 to McGlothlin et al., the entire disclosures of which are incorporated herein, address methods of vulcanization of dip-molded rubber articles with molten media baths.

Certain nitrosamines are carcinogenic and highly undesirable in dip molded products. U.S. Pat. No. 7,374,711 to McGlothlin et al., the entire disclosure of which is incorporated herein, addresses an accelerator-free vulcanization process to produce both carbon-sulfur and carbon-carbon crosslinking bonds. The vulcanization process being performed in the absence of any compounding components that contain secondary amine groups or any components that have a tendency to produce nitrosamines.

Molten media baths work well, but commercialization for large, high volume dip-molded goods such as condoms and gloves is difficult. Curing times as long as nine minutes or more require very long and large molten baths, which increase costs and/or create logistical issues for manufacturing facilities.

SUMMARY OF THE INVENTION

It has now been discovered that dip-molded articles of rubber need only be partially cured in a molten media bath. For example, latex is heated by immersion of a dip former into a heated liquid media bath to bring it to a desired curing temperature; e.g., 350° F. The molten media bath can be hotter than these temperatures to speed up the rate of temperature increase to get the latex to this desired curing temperature. Most preferably, the latex is not left in the bath any longer than to get to the desired curing temperature and not to fully cure the latex. Once the latex is at the desired curing temperature, it is immediately removed from the molten media bath and placed in a substantially oxygen free heating oven to complete curing. Alternatively, upon removal from the molten media bath, the latex is quenched in a quenching bath. Any unreacted peroxide in the latex is then extracted after separation from the dip former. Preferably, the molten media bath is free of nitrites.

In an embodiment of the invention, a method for the preparation of an article of rubber, the method comprises: dipping a forming member in a latex; withdrawing the forming member from the latex in a manner to leave a film of the latex over an outer surface of the forming member; immersing the forming member with the latex film thereon in a chemically inert liquid bath, for a duration of time, to partially cure and heat the latex film to a predetermined temperature, wherein the duration of time is less than a time it would take to fully cure the latex film; withdrawing the forming member from the chemically inert liquid bath; placing the forming member with the partially-cured latex film into a substantially oxygen free oven maintained at or above the predetermined temperature to fully cure the latex film; and separating the cured latex film from the forming member. The chemically inert liquid bath is a nitrite free salt bath. The latex can comprise a rubber and an organic peroxide, wherein the organic peroxide is dicumyl peroxide or alpha-bis(t-butylperoxy)diisopropylbenzene. The duration of time is less than or equal to six half-lives of the organic peroxide, four half-lives of the organic peroxide, or one half-life of the organic peroxide. The predetermined temperature is 350° F. plus or minus 25° F.

In another embodiment of the invention, a dip-molded article of a rubber is formed by a method comprising: dipping a forming member in a latex; withdrawing the forming member from the latex in a manner to leave a film of the latex over an outer surface of the forming member; immersing the forming member with the latex film thereon in a chemically inert liquid bath, for a duration of time, to partially cure and heat the latex film to a predetermined temperature, wherein the duration of time is less than the time it would take to fully cure the latex film; withdrawing the forming member from the chemically inert liquid bath; placing the forming member with the partially-cured latex film into a substantially oxygen free oven maintained at or above the predetermined temperature to fully cure the latex film; and separating the cured latex film from the forming member. The chemically inert liquid bath is a nitrite free salt bath. The latex can comprise a rubber and an organic peroxide, wherein the organic peroxide is dicumyl peroxide or alpha-bis(t-butylperoxy)diisopropylbenzene. The duration of time is less than or equal to six half-lives of the organic peroxide, four half-lives of the organic peroxide, or one half-life of the organic peroxide. The dip-molded article is a surgical glove, examination glove, or condom.

In yet another embodiment of the invention, a dip-molded article of a rubber is formed by a method comprising: dipping a forming member in a latex comprising a rubber and an organic peroxide; withdrawing the forming member from the latex in a manner to leave a film of the latex over an outer surface of the forming member; immersing the forming member with the latex film thereon in a chemically inert liquid bath, for a duration of time, to partially cure and heat the latex film to a predetermined temperature, wherein the duration of time is less than the time it would take to fully cure the latex film; withdrawing the forming member from the chemically inert liquid bath; quenching the forming member with the partially-cured latex film; separating the cured latex film from the forming member; and extracting residual and unreacted organic peroxide from the separated cured latex film. The chemically inert liquid bath is a nitrite free salt bath. The organic peroxide is dicumyl peroxide or alpha-bis(t-butylperoxy)diisopropylbenzene. The duration of time is less than or equal to six half-lives of the organic peroxide, four half-lives of the organic peroxide, or one half-life of the organic peroxide. The dip-molded article is a surgical glove, examination glove, or condom. The predetermined temperature is 350° F. plus or minus 25° F.

Among the many advantages of this invention is that completion of curing is facilitated in a simpler, less expensive hot air (gas) oven (or via a quenching bath and peroxide extraction process) as opposed to a lengthy molten media bath. This makes it much easier to convert an existing glove or condom production line into one that can process peroxide cure materials.

The foregoing, and other features and advantages of the invention, will be apparent from the following, more particular description of the preferred embodiments of the invention and the claims.

DETAILED DESCRIPTION OF EMBODIMENTS

Further features and advantages of the invention, as well as the structure and operation of various embodiments of the invention, are described in detail below.

The liquid bath, e.g., molten media bath, in which the dip former and film are immersed subsequent to the dip stage of the process, is a heated liquid that provides rapid heat transfer to the film. Further properties of liquid media that are most desirable and therefore preferred for this purpose are the lack of a tendency to migrate or diffuse into the film on the dip former (unless the medium itself is a desirable constituent of the film), the quality of being stable with respect to the surrounding environment (both the atmospheric environment and the rubber-forming material as well as the various species that may be compounded with the material), and the quality of remaining liquid at the vulcanization temperature. Examples of liquid media that can be used for this purpose are molten inorganic salts, oils, glycols, liquified metals, water, and brine solutions. Preferred among these are molten inorganic salts, silicone oils, and glycols, and the most preferred are molten inorganic salts. Examples of suitable molten inorganic salts are nitrates, carbonates, sulfates, phosphates, and halides of potassium, sodium and lithium, as well as combinations of salts of this group. In a preferred embodiment of the invention, a liquid salt bath comprising potassium nitrate and lithium nitrate is used.

As noted above, some nitrosamines are carcinogenic and highly undesirable in dip molded products. Accordingly, it is preferable to use a molten media bath that contains no nitrites. It was previously thought that the use of organic peroxides instead of traditional rubber accelerators would prevent the formation of nitrosamines. Moreover, the latex dipping industry generally assumed that the elimination of secondary amine-containing accelerators and other compounding chemicals prevented the formation of nitrosamines in dipped rubber articles. However, it has been discovered that these assumptions were incorrect; detectable levels of nitrosamines were found to be present in films when nitrites were present in the liquid bath. Accordingly, in a preferred embodiment to the invention, nitrites are not included in the liquid bath.

This invention is applicable to a wide range of rubber and rubber substitute compositions, including both lattices and organic solutions, thermoplastic elastomers, and thermoplastic polyurethanes.

Of the lattices, the one most commonly used is natural rubber. Natural rubber can be obtained from several sources, including *Hevea brasiliensis, Parthenum argentatum* (commonly known as "guayule"), *Taraxacum officinale*, and *Ficus elastica* rubber trees. Natural rubber latex is available in several grades, including high ammonia latex, low ammonia latex, and others. All such varieties are suitable for use in the present invention. This invention also extends to natural rubber lattices that have been processed to reduce the amount of proteins present in the lattices. Some of these processes include centrifuging to separate and remove water, and others include double centrifuging, in which an initial centrifuging is followed by the addition of water and a second centrifuging. Still other processes involve the use of enzymes to digest the proteins.

Synthetic rubber lattices in general are likewise usable in the practice of this invention. Examples are polyisoprene, ethylenepropylene-diene terpolymer, styrene isoprene rubber, styrene butadiene rubber, styrene isoprene butadiene rubber, polybutadiene rubber, polychloroprene, nitrite rubber, styrene block copolymers, silicone rubber, and butyl rubber. This invention also extends to polymer dispersions that are used in a manner similar to rubber lattices. One example is an aqueous dispersion of a polyurethane thermoplastic elastomer. For these dispersions, embodiments of the present invention that use curing systems other than those that are sulfur-based can be used. Polyurethane products such as medical examination gloves that are formed by the process of this invention exhibit increased resistance to solvents.

In addition to lattices and polymer dispersions, the present invention also applies to organic solutions. The organic solvents used in forming these solutions are any solvents that are inert to the rubber, rubber substitute or polymer, and that are readily removable from the dip-molded film by evaporation. The solvent is preferably an aliphatic hydrocarbon, saturated or unsaturated, linear, branched or cyclic, or ethers, esters, alcohols or amines. Typical solvents are aliphatic hydrocarbons containing five to eight carbon atoms, such as pentane, pentene, hexane, heptane, cyclohexane, and cyclopentane, and heterocyclic compounds such as tetrahydrofuran.

A wide variety of vulcanizing agents can be used in the practice of this invention. Useful vulcanizing agents include organic peroxides, sulfur-containing compounds, selenium-containing compounds, and tellurium-containing compounds. Organic peroxides, for example, may be used singly or in combination, and the most common types are diacyl peroxides, peroxyketals, and dialkyl peroxides. Preferred organic peroxides are the dialkyl peroxides, particularly dicumyl peroxide. Other useful dialkyl peroxides are 2,5-dimethyl-di-(t-butylperoxy) hexane; di-t-butylperoxide; t-butylcumyl-peroxide; bis(t-butylperoxyisopropyl)benzene; butyl4,4-bis(t-butylperoxy)valerate; 2,5-bis(t-butylperoxy)-2,5-dimethylhexane; 2,5-bis (t-butylperoxy)-2,5-dimethyl-3-hexane; t-butyl3-isopropenylcumyl peroxide; bis (3-isopropenylcumyl) peroxide; 1,1-bis(t-butylperoxy)-3,3, 5-trimethylcyclohexane; t-butylperoxybenzoate, and bis(2, 4-dichlorobenzoyl) peroxide.

In addition to dicumyl peroxide, alpha-bis(t-butylperoxy) diisopropylbenzene ("Alpha") is a preferred peroxide. The advantage of Alpha as compared to dicumyl peroxide is that it produces less odiferous off gas products in the cured latex films. Dicumyl peroxide leaves behind acetophenone, which has a strong odor. The use of hot air after a salt bath allows for efficient "airing out" of the peroxide breakdown products.

The present invention is very useful for peroxide curing in that it makes it commercially feasible to cure latex films. For dip-molded parts that do not contain peroxides, the present invention is also useful. Most accelerator/sulfur hot air cured films have less than desirable latex particle integration and have poor uniform crosslinking. When films without peroxide are cured in a molten salt bath, the particle integration and uniformity of cross linking throughout the cured film is far superior to that of film just cured in a hot air oven. The molten salt bath essentially melts the particles together while curing. By using just a hot air oven, the particles are just sintered or fused together on their surfaces. Others have gone to great pains to optimize the particle integration and uniform crosslinking in latex films. U.S. Pat. Nos. 8,087, 412; 8,464,719; 9,074,027; and 9,074,029, all of the entire disclosures of which are incorporated herein by reference, are examples that require meticulous attention to process details and still are not as effective in integrating latex particles as is the molten media batch process.

Coagents and other additives are often used in conjunction with the organic peroxides to achieve products having particular properties. Certain coagents also add to the crosslinking efficiency of the peroxides by causing a single peroxide radical to produce more than one carbon-carbon crosslink. Coagents can also be integrated into the polymer network by covalent bonds to enhance certain properties of the polymer, such as elongation and tear strength. Some of these coagents are based on acrylate and methacrylate chemistry. All, however, are suitable for inclusion in the methods and products of the present invention. Examples of suitable coagents are multifunctional salts of acrylic and methacrylic acids. Of this group of coagents, SARET 634 (whose primary ingredient is zinc dimethacrylate) and SARET 521 (whose primary ingredients are difunctional acrylate esters) are the most preferred. Trimethylolpropane trimethacrylate is another example.

Sulfur-based vulcanization systems include both small sulfur-containing molecules and sulfur-containing polymers. Examples of sulfur-based vulcanization chemicals are: mercaptothiazoles, for example, 2-mercaptobenzothiazole and its salts, notably its zinc salt; thiuram sulfides and disulfides, for example, tetraethylthiuram monosulfide, tetrabutylthiuram monosulfide, tet-ramethylthiuram disulfide, and tetra-ethylthiuram disulfide; guanidines; thiourea and substituted thioureas; thiocarbanilides and substituted thiocarbanilides, for example, o-dimethyl-thiocarbanilide and its isomers and alkyl homologs; zinc alkyl dithiocarbamates, for example, zinc dimethyl dithiocarbamate, and accelerators containing these materials; sodium or potassium dimethyl dithiocarbamate selenium dialkyl dithiocarbamates, for example, selenium diethyldithiocarbamate; 2-benzothiazyl-N,N-di-ethylthiocarbamyl sulfide xanthates such as dibutyl xanthogen disulfide and xanthogen polysulfide; alkyl phenol sulfides; dipentamethylene tetrasulfide; sulfur-containing polymers such as Thiokol VA-3; 4,4-dithiomorpholine; and miscellaneous disulfides such as bensothiazyl disulfide and bis (dimethylthiocarbamoyl) disulfide.

When the dip-molded articles of this invention are intended for use in contact with human skin, the preferred compounding ingredients are those that produce films that are biocompatible. Examples of compounding ingredients that serve this purpose for sulfur-vulcanized systems are xanthogen compounds such as diisopropyl xanthogen polysulfide, dibenzyldithiocarbamate, and higher alkyl zinc dithiocarbamates. For peroxide vulcanized systems, a preferred compounding ingredient is dicumyl peroxide or Alpha. Again, Alpha does not produce many malodorous off gases in comparison to dicumyl peroxide.

Reinforcing agents and other additives are also included in some embodiments of the invention. Examples of reinforcing agents are fumed silica, carbon black, graphene, graphene oxide, and chopped fibers. The use of cut fibers improves the tear strength of medical gloves and the use of fumed silica improve the tear strength of dipped films. Antioxidants and antiozonants may also be included to protect against environmental aging. Pigments and dyes may also be included, as may any of the other additives known to those skilled in the art of the formulation and manufacture of rubber devices.

An illustrative procedure for latex dip molding and curing in accordance with the present invention is as follows:

1. Either a natural rubber or a synthetic rubber latex is compounded with vulcanizing agent(s) and possibly an antioxidant, a stabilizer or both. If organic peroxide vulcanization is used, it will often be sufficient to simply add to the latex a dispersion that contains an organic peroxide.

2. Prevulcanization of the latex at this stage is optional and not required for all embodiments of this invention. When used, prevulcanization can improve the wet gel strength.

3. A dip former is optionally coated with a chemical coagulant by dipping the former into a bath of a coagulant-containing liquid, then withdrawing the former and drying it.

4. The dip former, with or without the coagulant coating, is dipped in a bath filled with the compounded latex.

5. The dip former is slowly withdrawn from the bath. If the former had a coagulant coating, it now has a wet latex gel on its surface. If no coagulant coating was applied, the former will have a liquid latex film on its surface.

6. Excess water in the latex film on the dip former surface is removed, generally by evaporation in a hot air convection oven with either sweep gas or a partial vacuum. The process can be supplemented with infrared, microwave, or radiofrequency radiation, or any other type of energy to expedite the evaporation. Vacuum drying is advantageous since it avoids the need for exposure of the dried latex to air at an elevated temperature prior to vulcanization.

7. The latex is heated by immersion of the dip former into the heated liquid media bath to bring it to a desired curing temperature. A preferred curing temperature range for the full scope of this invention is about 235° F. to 600° F. For polychloroprene and styrenebutadiene rubber, a preferred temperature range is about 300° F. to about 600° F., while for natural rubber a preferred temperature range is about 235° F. to 500° F. The molten media bath can be greater than these temperatures to speed up the rate of temperature increase to get the latex to the desired curing temperature; e.g., 350° F. Experiments have shown that this can be done in under about one minute time. Most preferably, the latex is not left in the bath any longer than to get to the desired curing temperature and not to fully cure the latex. The present invention exposes the latex to the media bath for a duration much less than prior art systems. For example, prior art methods leave the latex in the media bath for nine minutes at 350° F. to achieve a complete cure. Here, the molten media bath only partially cures the latex. Where the latex includes an organic peroxide, the duration of time in the molten salt bath is measured in half-lives of the organic peroxide. For example, at a temperature of 350° F., dicumyl peroxide has a half-life time of approximately one minute. In a preferred embodiment of the invention, the duration of time is less than or equal to one half-life. In another embodiment of the invention, the duration of time is less than or equal to four half-lives. In yet another embodiment of the invention, the duration of time is less than or equal to six half-lives. In another embodiment of the invention, the duration of time is less than nine half-lives.

8. Upon the latex being brought up to the desired curing temperature via the molten media bath, the dip former with the partially-cured latex film is immediately removed from the bath and its temperature is maintained at the desired curing temperature in a low/no oxygen heating oven for a period of time sufficient to react ninety (90) percent or more of the organic peroxide. The oven can be any type of oven such as a hot gas oven, a heated chamber, a plenum, or any type of enclosure containing a low oxygen or oxygen free heated environment. In other words, the period of time is equal to about nine (9) half-lives of the peroxide (minus the time spent in the molten bath), which eliminates virtually all of the peroxide as shown in the following table.

| Half-Lives | % Cured |
| --- | --- |
| 1 | 50.0 |
| 2 | 75.0 |
| 3 | 87.5 |
| 4 | 93.8 |
| 5 | 96.9 |
| 6 | 98.4 |
| 7 | 99.2 |
| 8 | 99.6 |
| 9 | 99.8 |
| 10 | 99.9 |

The net effect of this step is to very substantially reduce the time in the salt bath by a significant amount; e.g., ninety (90) to ninety-five (95) percent or more. In embodiments of the invention, the low/no oxygen environment is facilitated via a "zero air" gaseous environment or inert gas environment such as, but not limited to helium, nitrogen, and/or argon, or reduced oxygen air. Nitrogen is preferred due to its wide availability. For low oxygen air, the flue gas from natural gas or propane combustion can be used both to maintain temperature and to eliminate oxygen. A low oxygen environment is one without enough oxygen to significantly react with any remaining peroxide.

9. After curing of the latex, the rubber articles are removed from the oven and cooled; for example, in air or a stream of water. Water may be used to rinse off any excess solidified heat transfer medium such as solidified salt.

10. The vulcanized latex article is manually or mechanically stripped from the dip former.

In an alternative embodiment of the invention, curing time is reduced by actively quenching the dip former with latex film before curing is complete. Quenching can be an alternative to the low/no oxygen heating oven above entirely (or to reduce the time in the heating oven). Quenching eliminates atmospheric oxygen from reacting with residual peroxide, which creates tackiness via oxidation of the rubber. For example, a 2.4 phr of dicumyl peroxide formulation can be cured for one minute, which is the half-life of dicumyl peroxide at 350° F. Rapidly quenching the reaction of the formulation (when heated) after one minute provides a fully cured film, but with a residual level of 1.2 phr of unreacted dicumyl peroxide in the rubber, which is not desirable. After the dipped goods are stripped, residual unreacted dicumyl peroxide is extracted via a soxlet extraction method, a critical $CO_2$ extraction, ethyl acetate soaking method, or a rubber extraction method, the identification and implementation of all of which are apparent to one of ordinary skill in the art.

In another embodiment of the invention, a layer of molten salt is allowed to stay on the outside of the rubber film to form a barrier between the oxygen containing environment and the still-curing rubber film. If desired, it would be further possible to heat the molten salt bath and the dip former to a temperature well above the normal curing temperature of the rubber and to then leave on a molten salt film or placement of the former/mandrel into a low/no oxygen heating oven without actually bringing the new environment up to the normal 350° F. temperature. As the "overheated" former cools in the lower temperature atmosphere, the temperature is still high enough to allow for complete curing of up to about nine (9) half-lives.

An illustrative procedure for solvent dip molding and curing in accordance with the present invention is as follows:

1. Solid granules of synthetic or natural rubber elastomer are dissolved in a suitable solvent to form a cement. Suitable compounding agents are dispersed or dissolved in the cement. Compounding agents similar to those used in the latex processes, including organic peroxides, can be used.

2. No prevulcanization is necessary, as all compounding agents are uniformly dispersed in the cement. The cement is placed in a dip tank, and a dip former is dipped in the cement.

3. The dip former is slowly withdrawn from the dip tank to leave a film of the cement over the surface of the dip former.

4. Solvent is evaporated from the dip former to leave a uniform polymer film on the surface. Removal of the solvent can be achieved by ambient or hot air drying.

5. The latex is heated by immersion of the dip former into the heated liquid media bath to bring it to a desired curing temperature. A preferred curing temperature range for the full scope of this invention is about 235° F. to 600° F. For polychloroprene and styrenebutadiene rubber, a preferred temperature range is about 300° F. to about 600° F., while for natural rubber a preferred temperature range is from about 235° F. to 500° F. The molten media bath can be greater than these temperatures to speed up the rate of temperature increase to get the latex to the desired curing temperature; e.g., 350° F. Experiments have shown that this can be done in under about one minute time. Critically, the latex is not left in the bath any longer and not to fully cure the latex.

6. Upon the latex being brought up to the desired curing temperature via the molten media bath, the dip former with the partially-cured latex film is immediately removed from the bath and its temperature is maintained at the desired curing temperature in a low/no oxygen heating oven for a period of time sufficient to react ninety (90) percent or more of the organic peroxide as noted above.

7. After curing of the latex, the dip former is withdrawn from the oven and cooled in air or a stream of water.

8. The dip former is then soaked in water to help break the adhesion between the film and the dip former.

9. The vulcanized latex article is manually or mechanically stripped from the dip former.

While the present invention virtually eliminates the need for prevulcanization and maturation of the compounded latex or solution, prevulcanization is useful with lattices that would otherwise have an exceptionally low wet or dry gel strength. Prevulcanization can be done by any conventional method. Such methods include, but are not limited to, sulfur prevulcanization, peroxide prevulcanization, and prevulcanization by high energy irradiation, all of which may be performed as they are in the prior art. Good wet gel strength is useful in preventing cracks from forming in the film as the film is being dried. In the case of natural rubber, both wet and dry gel strengths are generally adequate without prevulcanization. The gel strengths of some synthetic latices are lower, however, and prevulcanization may improve the processing, but is not essential. Prevulcanization by high energy irradiation can also serve to reduce the amount of vulcanization chemicals needed and hence the levels of undesirable residual chemicals in the final product.

It is often useful to determine the extent to which a dipped film or article has been vulcanized. A commonly used method is to cut out a circular disk of the cured film and measure the change in diameter upon immersion of the disk in a solvent bath. Similar test methods are available for other types of vulcanized polymers, and are well known to those skilled in the art.

The following examples are offered for purposes of illustration, and are not intended to limit the scope of the invention.

Example 1

Process According to the Invention: Natural Rubber Latex

This example illustrates the process of the present invention. A coagulant solution in ethanol was used, containing approximately twenty (20) percent calcium nitrate, and 0.5 percent Igepal C0-630, all by weight, the balance denatured ethanol. To 1 kg of natural rubber latex was added 19.5 g of the dicumyl peroxide emulsion, and the resulting composition was mixed under medium shear for thirty minutes on a laboratory mixer. In addition, fumed silica was added at 2 phr in the form of a fifteen (15) percent (by weight) aqueous dispersion. After thirty minutes of mixing, the solution was rolled for thirty minutes on a laboratory roll mill, then degassed for ten minutes at 0.3 atmosphere absolute pressure. This yielded approximately 1 liter of natural rubber latex formulated with 1.3 phr dicumyl peroxide. The glass former was dipped into the coagulant solution, then dried for five minutes at 40° C., then slowly dipped into the formulated latex where the former was allowed to dwell for five seconds. The former was then slowly withdrawn and dried at 60° C. for sixty minutes. Once dried, the former and its adherent film were immersed in a molten salt bath for one minute at 350° F. (177° C.) and then placed into a low/no oxygen heating oven to complete curing. The film was then rinsed, stripped, and readied for tensile testing. The film appeared translucent-to-clear and slightly amber in color and more transparent than many sulfur-vulcanized rubber films. The film produced in this example is expected to meet the necessary tensile strength requirements for both surgical gloves and condoms.

Example 2

Process According to the Invention: Polychloroprene

This example illustrates the process of the present invention as applied to polychloroprene, using procedures similar to those of the preceding examples. The polychloroprene was a latex containing weight percent solids, and is sold commercially as NEOPRENE 750.

A dicumyl peroxide emulsion was added to the latex to attain a formulated latex containing 0.1 phr dicumyl peroxide. Also added to the latex was fumed silica (reinforcing agent), added as a fifteen (15) weight percent aqueous dispersion to achieve a level of 3 phr fumed silica.

The glass former was first dipped into an aqueous coagulant solution, which contained 35% calcium nitrate, 0.5% IGEPAL C0-630 surfactant, both by weight, the balance dionized water, then allowed to dry. The former was then dipped in the compounded latex and allowed to dwell in the latex for five seconds, then slowly withdrawn and dried at 60° C. for sixty minutes. After drying, the former with latex film was immersed in a molten salt bath having the same composition as the baths used in the preceding example, for one minute at 350° F. (177° C.) and then placed in a low/no oxygen heating oven to complete curing. The former and film were then rinsed, stripped, and readied for tensile testing. The resultant latex film was transparent and amber in color, and sufficient to pass the ASTM standard D-3577-98 for synthetic rubber surgical gloves.

Example 3

Process According to the Invention: Polyurethane

This example illustrates the process of the present invention as applied to polyurethane, and specifically, in the modification of thermoplastic polyurethane films after the films have been formed.

Two solvent dip molding solutions were prepared. The first consisted of (fifteen) (15) weight percent thermoplastic polyurethane and eighty-five (85) weight percent tetrahydrofuran. A control film (in the form of a condom) was prepared by dipping the form into an organic solution, as described in U.S. Pat. No. 4,954,309, to McGlothlin et al., the entire disclosure of which is incorporated herein by reference. After drying, the polyurethane condom thus formed was stripped from the former. The second dip molding solution was formed by adding 0.5 phr dicumyl peroxide to the first solution, and a second dip-molded condom was prepared in a manner essentially identical to the first, except that the dipped and dried condom was then immersed for one minute in a molten salt bath (identical to those used in the preceding examples) at 350° F. (177° C.) and transferred to a low/no oxygen heating oven to complete curing.

Portions of both the control condom and the test condom were subjected to a solvent resistance test. According to this test, both films were immersed in tetrahydrofuran. The control film dissolved entirely when immersed in the tetrahydrofuran, while the second, which had been crosslinked by the dicumyl peroxide treatment, did not dissolve but instead swelled significantly. This test illustrates the improvement in properties of dip-molded articles made of polyurethane (as representative of thermoplastic elastomers in general) as a result of the process of the present invention.

Example 4

Process According to the Invention: Prevulcanized Natural Rubber Latex

This example illustrates the process of the present invention applied to two prevulcanized natural rubber lattices, one by sulfur and the other by radiation. The sulfur prevulcanized latex was sixty (60) percent solids REVULTEX HLA-21. The radiation-prevulcanized latex was "RVNRL." Both lattices are noted for their low levels of residual chemicals and hence their low toxicity profiles. Because of the low toxicity profiles, the tensile strengths of these materials are lower than those of many other natural rubber lattices. Standard clear-glass condom formers, 32 mm in diameter, as used in all preceding examples were used as dip formers. Four compounded latices were used, as follows:
  1. REVULTEX HLA-21 (sulfur-prevulcanized latex) as supplied by Revertex Americas.
  2. REVULTEX HLA-21 (sulfur-prevulcanized latex) as supplied by Revertex Americas, supplemented with dicumyl peroxide to 1.0 phr.
  3. RVNRL as supplied by Guthrie Latex, Inc.
  4. RVNRL as supplied by Guthrie Latex, Inc., supplemented with dicumyl peroxide to 1.0 phr.

One condom was formed from each of these three lattices, using the coagulant solution and the dipping and drying procedures of Example 3. All were then dried for sixty minutes at 60° C. The condoms formed from lattices that did not contain dicumyl peroxide were further dried for 45 minutes at 150° F. (66° C.) in a hot air oven, powdered, stripped, and set aside. The condoms formed from lattices that did contain dicumyl peroxide were further processed by immersion in a molten salt bath of the same description as those used in the preceding examples, for one minute at 350° F. (177° C.) and placed low/no oxygen heating oven to complete curing. All four condoms were rinsed, powdered, and stripped. The properties of the dip-molded condoms of both methods of prevulcanization, sulfur-based and radiation, are enhanced by postvulcanization in accordance with the present invention.

Example 5

Process According to the Invention: Addition of Vulcanizing Agent by Imbibition for Secondary Postvulcanization This example illustrates that aspect of the present invention in which a vulcanized and fully formed dip-molded article is given a secondary postvulcanization by first immersing the article in a solution of a vulcanizing agent to absorb the agent from the solution and then re-curing the article following the absorption. The rubber material used in this example was synthetic polyisoprene rubber, supplied as a ten (10) percent solids solution in n-hexane. The polyisoprene was NATSYN 2200, and was dissolved in the hexane by agitating with a medium-shear laboratory mixer. The resulting solution was split into two batches, and the first was supplemented by the addition of dicumyl peroxide to 1.5 phr while the second was supplemented by the addition of dicumyl peroxide to 2.0 phr. Stainless steel dipping mandrels with outside diameters of 0.091 inch (0.23 cm) were dipped in the solutions, withdrawn, air dried and re-dipped in a sequence that was repeated approximately seven times to build up a single wall balloon thickness of approximately 0.010 inch (0.0254 cm). After thorough drying in a warm air oven to remove essentially all of the solvent, the portions of the dipping formers that were coated with the dried mixture of polyisoprene and dicumyl peroxide were immersed in a hot molten salt bath (the same as that used in the preceding examples) for one minute at 350° F. (177° C.) and placed in a low/no oxygen heating oven to complete curing. The resulting balloons were rinsed in water, powdered with corn starch, and removed from the dipping formers. Each balloon was then cut into segments approximately 1 cm in length to form right heart catheter balloons.

Six of the balloons formed from the 1.5 phr dicumyl peroxide dipping solution were immersed for thirty minutes in an imbibing solution consisting of dicumyl peroxide dissolved in ethyl acetate, the solution having a sufficient concentration and volume to raise the dicumyl peroxide content of the balloons by 0.5 phr. The balloons were then removed from the solution and thoroughly air-dried in a warm air oven to remove essentially all ethyl acetate. The balloons were then immersed in a molten salt bath (as described in the preceding examples) for one minute at 350° F. (177° C.) and placed in a low/no oxygen heating oven to complete curing. The balloons were then removed, rinsed in water, dried, and powdered with corn starch. An unexpected improvement in physical properties was achieved by a two-stage postvulcanization achieved by the imbibition of a vulcanizing agent by an already-formed dip-molded rubber article, followed by vulcanization in a hot liquid bath and oven, as compared to a single-stage postvulcanization at the same level of vulcanizing agent.

Example 6

Comparison Using Natural Rubber Latex: Hot Liquid Medium Cure According to the Invention Vs. Hot Air Cure of Prior Art This example demonstrates the improvement offered by the present invention. Natural rubber latex supplemented with a sulfur-based curing system was used in this comparison.

Natural rubber latex (sixty percent (60%) solids) was supplemented with a curing system bearing the name OCTACURE 590 in an amount which, according to the supplier, results in a compounded latex containing 2 phr zinc oxide, 1.65 phr sulfur, 0.5 phr zinc-2-mercaptobenzothiazole, and 0.75 phr of an unspecified antioxidant. The latex was degassed, and two condoms were prepared from the latex in the manner described in Example 1, involving the use of the coagulant described in that example. One of the condoms while still on the former was then vulcanized in hot air for 45 minutes at 100° C., and then for an additional sixty minutes at 110° C. The second condom, also while still on the former, was dried for forty-five minutes at 100° C., then immersed in a molten salt bath of the same description as those used in the preceding examples for one minute at 350° F. (177° C.) and then placed in a low/no oxygen heating oven to complete curing. The present invention is applicable to natural latex rubber without the need for prevulcanization.

Example 7

Application of the Invention to Latex Mixtures

This example demonstrates the application of the process of the invention to a mixture of lattices.

A mixture was prepared by combining equal parts by weight of Shell IR-307 synthetic polyisoprene latex and NEOPRENE 750 polychloroprene latex. A dicumyl peroxide dispersion was added to achieve a latex containing 0.7 phr dicumyl peroxide. One condom was produced from this latex, using the method described in Example 1, then immersed in a molten salt bath of the same description as those used in the preceding examples for one minute at 350° F. (177° C.), placed in a low/no oxygen heating oven to complete curing, then rinsed and powdered. The condom was opaque and amber in color.

The foregoing is offered primarily for purposes of illustration. It will be readily apparent to those skilled in the art that the materials and their proportions, as well as the operating conditions, procedural steps and other parameters of the inventions described herein may be further modified or substituted in various ways without departing from the spirit and scope of the invention.

We claim:

1. A method for the preparation of an article of rubber, the method comprising:
   dipping a forming member in a latex;
   withdrawing the forming member from the latex in a manner to leave a film of the latex over an outer surface of the forming member;
   immersing the forming member with the latex film thereon in a chemically inert liquid bath, for a duration of time, to partially-cure and heat the latex film to a predetermined temperature, wherein the duration of time is less than a time it would take to fully cure the latex film;
   withdrawing the forming member from the chemically inert liquid bath;
   placing the forming member with the partially-cured latex film into a substantially oxygen free oven maintained at or above the predetermined temperature to fully cure the latex film; and
   separating the cured latex film from the forming member.

2. The method of claim 1, wherein the chemically inert liquid bath is a nitrite free salt bath.

3. The method of claim 1, wherein the latex comprises a rubber and an organic peroxide.

4. The method of claim 3, wherein the organic peroxide is dicumyl peroxide or alpha-bis(t-butylperoxy)diisopropylbenzene.

5. The method of claim 4, wherein the duration of time is less than six half-lives of the organic peroxide.

6. The method of claim 5, wherein the duration of time is less than or equal to four half-lives of the organic peroxide.

7. The method of claim 6, wherein the duration of time is less than or equal to one half-life of the organic peroxide.

8. The method of claim 1, wherein the predetermined temperature is 350° F. plus or minus 25° F.

9. A method for forming a dip-molded article of a rubber comprising:
   dipping a forming member in a latex comprising a rubber and an organic peroxide;
   withdrawing the forming member from the latex in a manner to leave a film of the latex over an outer surface of the forming member;
   immersing the forming member with the latex film thereon in a chemically inert liquid bath, for a duration of time, to partially-cure and heat the latex film to a predetermined temperature, wherein the duration of time is less than the time it would take to fully cure the latex film;
   withdrawing the forming member from the chemically inert liquid bath;
   quenching the forming member with the partially-cured latex film thereon to form a cured latex film;
   separating the cured latex film from the forming member; and
   extracting residual and unreacted organic peroxide from the separated cured latex film.

10. The method of claim 9, wherein the chemically inert liquid bath is a nitrite free salt bath.

11. The method of claim 9, wherein the organic peroxide is dicumyl peroxide or alpha-bis(t-butylperoxy)diisopropylbenzene.

12. The method of claim 11, wherein the duration of time is less than six half-lives of the organic peroxide.

13. The method of claim 12, wherein the duration of time is less than or equal to four half-lives of the organic peroxide.

14. The method of claim 13, wherein the duration to time is less than or equal to one half-life of the organic peroxide.

15. The method of claim 9, wherein the dip-molded article is a surgical glove, examination glove, or condom.

16. The method of claim 9, wherein the predetermined temperature is 350° F. plus or minus 25° F.

* * * * *